United States Patent [19]  [11]  4,309,415
Horrobin  [45]  Jan. 5, 1982

[54] METHOD AND COMPOSITION FOR TREATING INFLAMMATORY DISORDERS

[75] Inventor: David F. Horrobin, Montreal, Canada

[73] Assignee: Verronmay Limited, London, England

[21] Appl. No.: 29,058

[22] Filed: Apr. 11, 1979

[30] Foreign Application Priority Data

Apr. 11, 1978 [GB] United Kingdom ............... 14172/78
Sep. 4, 1978 [GB] United Kingdom ............... 35437/78

[51] Int. Cl.³ .................... A61K 45/02; A61K 31/54; A61K 33/30; A61K 31/20
[52] U.S. Cl. ..................................... 424/85; 424/145; 424/246; 424/256; 424/270; 424/271; 424/274; 424/285; 424/289; 424/312; 424/318
[58] Field of Search ............... 424/312, 270, 145, 85, 424/289, 274, 256, 285, 271, 246, 318

[56] References Cited

U.S. PATENT DOCUMENTS 3,949,072 4/1976 Tenta ................................. 424/145

OTHER PUBLICATIONS

Willis et al.-Prostaglandins, Dec. 25, 1974, vol. 8, No. 6.
Physicians' Desk Reference 1968 ed., p. 580.
Chemical Abstracts, , vol. 77, 1972, 39210, vol. 83, 15500a, vol. 83, 26534r.

Primary Examiner—Frederick E. Waddell
Attorney, Agent, or Firm—Cushman, Darby & Cushman

[57] ABSTRACT

Compositions and use of γ-linolenic acid and related materials with (i) zinc, β-lactam antibiotics or other materials enhancing physiological 1-series PG synthesis and/or (ii) colchicine, Vinca alkaloids or other materials enhancing physiological synthesis of thromboxane A2, for treatment of inflammatory disorders.

37 Claims, No Drawings 4,309,415

METHOD AND COMPOSITION FOR TREATING INFLAMMATORY DISORDERS

FIELD OF THE INVENTION

This invention relates to the treatment of certain diseases and disorders primarily, but not exclusively, in the field of human medicine and to compositions for use therein.

GENERAL BACKGROUND

Considerable interest has been shown in recent years in the use of prostaglandin (PG) precursors in medicine.

For various reasons it is not practical to administer naturally-occurring prostaglandins such as PGE 1 and PGE 2 to patients. Consequently, considerable attention has focussed on the use of prostaglandin precursors including linoleic acid, γ-linolenic acid (GLA) and dihomo-γ-linolenic acid (DGLA).

Conversion of these materials in the body is believed to be as shown in the following diagram.

The broad outline of this pathway is well known, but the details of control, inhibition and enhancement are shown as the present inventor believes them to operate. The pathway is now discussed with particular reference to treatment of inflammatory disorders according to the invention. This discussion is given in the belief that it elucidates the invention, but it is not intended that the invention should be limited by what is believed to be the reason for its effectiveness.

A major function of essential fatty acids (EFAs) is to act as precursors for prostaglandins (PGs), 1 series PGS being formed from dihomo-γ-linolenic acid (DGLA) and 2 series PGs from arachidonic acid (AA). DGLA and AA are present in food in only small quantities, and the major EFA in food is linoleic acid which is first converted to γ-linolenic acid (GLA) and then to DGLA and AA. The conversion of linoleic acid to GLA is blocked by a high fat and high carbohydrate diet, by ageing and by diabetes. Stores of AA in the body in the form of lipid esters are very large indeed. In contrast only small amounts of DGLA ester are present.

Thus the invention, in one aspect, serves to redress the 1-series PG depletion by administering γ-linolenic acid and/or other materials tending to enhance 1-series PG production. In another aspect, desirably combined with the first, it seeks to restore TXA2 production directly.

It has further recently been found that a critical factor in some inflammatory disorders, e.g. in the damage of myelin which occurs in multiple sclerosis, may be the entry of calcium into cells. This may damage mitochondria and activate destructive lysosomal enzymes. Thus, there is now evidence which indicates that the regulation of the immune response and also the control of intracellular calcium may be significant factors in the treatment of various inflammatory disorders, e.g. multiple sclerosis, Crohn's disease and other disorders listed below.

The present inventor has now found that colchicine is a substance which appears to be able to potentiate the removal of calcium by cells and thus may be able to control intracellular calcium. Colchicine may also inhibit formation of 2 series PG's and enhance formation of 1 series PG's. In a further aspect of the invention, therefore, in conjunction with correction in EFA balance, colchicine is administered to effect such control.

The relationship of this to EFA metabolism is discussed later.

In inflammatory disorders, production of 2 series PGs from arachidonic acid is greatly exaggerated. In inflammatory disorders these PGs are thought to contribute to the causation of the disease because steroids and aspirin-like drugs are both partially effective therapies, steroids blocking the conversion of AA esters to free AA and aspirin-like drugs blocking the conversion of free AA to endoperoxides which are intermediates in PG synthesis.

The overproduction of 2 series PGs implies that normal control of the PG synthetic pathway has been lost. Although control of this pathway is imperfectly understood two factors have been identified.

1. PGE1 is able to inhibit the formation of free AA from AA esters. This leads to the paradoxical fact that a partial EFA deficiency actually leads to increased formation of 2 series PGs, because DGLA stores are so much smaller than those of AA and a partial deficiency of EFAs will therefore lead to DGLA depletion first. This depletion will reduce formation of PGE1, remove the PGE1 control of AA and allow overproduction of 2 series PGs from the large AA stores.
2. An unstable product of AA metabolism, thromboxane A2 (TXA2), also feeds back to inhibit conversion of AA ester to free AA and possibly also of free AA to PG2 endoperoxides. Thus loss of TXA2 will also lead to overproduction of 2 series PGs. TXA2 and PGE1 thus cooperate in the regulation of formation of 2 series PGs and a fault in the formation of either will lead to adnormalities.

Thus for example the disorders of PG synthesis in inflammatory disorders can be accounted for by inadequate formation of PGE1 and/or TXA2.

The evidence for direct involvement of PGs in inflammatory disorders has been briefly mentioned. There is also indirect evidence that PGs may act by regulating—or failing to regulate—the calcium movements into and out of cells already mentioned above. The calcium concentration in cytoplasm is normally very low and there is now excellent evidence from many sources that a brief rise in cytoplasmic calcium concentration triggers a variety of cell events, including cell division and activation of lysosomes which contain destructive enzymes. Normally this calcium is very rapidly removed after this brief activation so terminating the event. PGs and related substances have specific actions on calcium and the present inventor has obtained evidence to suggest that TXA2 and PGF2α may be of critical importance. In particular, specific inhibition of TXA2 synthesis greatly prolongs the time taken for calcium to be removed from the cytoplasm after activation. Furthermore inhibition of TXA2 synthesis leads to increased formation of PGFα and PGE2 which can promote calcium entry into cells. There is thus good evidence that in this respect also PGE1 and TXA2 enhance one another's effects. In particular, in muscle the degree of contraction is related to the calcium concentration in the cytoplasm and muscle contraction is a measure of this calcium concentration. After inhibition of TXA2 synthesis the recovery from a contraction is greatly prolonged indicating slow removal of calcium. Further, inhibition of TXA2 synthesis can lead to a chronic state of partial contraction indicating the entry of calcium into the cytoplasm. PGF2α and PGE2 whose output is increased by inhibition of TXA2 synthesis also cause contraction indicating calcium entry into the cytoplasm.

Thus loss of TXA2 and PGE1 synthesis will lead to increased formation of 2 series PGs and entry of calcium into the cytoplasm. This calcium may activate cell division and also activate lysosomes whose destructive enzymes may play a large part in inflammation.

On general grounds there are therefore reasons to suppose that suppression of excess production of 2 series PGs will have desirable effects in inflammatory disorders. Currently available conventional methods of suppression are administration of steroids and aspirin-like drugs. However, while these may suppress overproduction of 2 series PGs they will exaggerate further any deficiencies in PGs of the 1 series and in TXA2, which may explain why they control symptoms but do not usually alter the long term course of the disease.

The present invention proposes a radically new approach which will control excess PG2 series production by restoring towards normal, or enhancing, the formation of either or both of 1 series PGs and TXA2.

The methods proposed for doing this are as follows:

1-Series PGs

To increase the available supply of precursors of 1 series PGs by providing adequate amounts of GLA or DGLA which will by-pass any metabolic block between LA and GLA. The GLA or DGLA may be either synthetic or found in natural products. The formation of 1 series PGs may be enhanced further by the administration of pharmacological agents with the GLA or DGLA. Agents which have this effect are listed later in the specification. They include penicillamine and levamisole which have both been used as anti-inflammatory agents in rheumatoid arthritis with a completely unknown mechanism of action.

TXA2

To enhance the formation of TXA2 by means of agents which specifically activate the enzyme which forms TXA2 from PG2 series endoperoxides. These agents also are listed later in the specification, and include colchicine and related compounds such as the Vinca alkaloids.

Direct evidence of effectiveness in inflammatory disorders treatments is given at the end of the specification.

There now follow some references to prior proposals for the use of $\gamma$-linolenic acid and like materials in medicine, and then a detailed statement of the present invention.

DESCRIPTION OF THE PRIOR ART

Prior art within this general area includes the following patents and papers.
(i) U.S. Pat. Nos. 3,993,775 (issued Nov. 23rd, 1976) and 4,058,594 (issued Nov. 15th, 1977) of John Williams, which described a method of providing an immunosuppressive effect in a patient undergoing organ or tissue transplant or suffering from multiple sclerosis comprising administration of a daily dosage of from 5 mg to 3 g of $\gamma$-linolenic acid or dihomo-$\gamma$-linolenic acid or a functional derivative thereof.
(ii) British Patent Specification No. 1,082,624 published Sept. 6th, 1967 (Calmic Limited), which discloses effectiveness of $\gamma$-linolenic acid in the treatment of vascular diseases.
(iii) McCormack, Neil and Sim (The Lancet, page 3)8, Sept. 3rd, 1977), who describe preliminary work on the use of an oil containing a mixture of linoleic acid and $\gamma$-linolenic acid (as triglycerides) in the treatment of rheumatoid arthritis.
(iv) Sim and McCraw (Thrombosis Research Volume 10, pages 385–397, 1977), who describe activity of the methyl esters of $\gamma$-linolenic acid and dihomo-$\gamma$-linolenic acid in vitro and in vivo on blood platelet function in non-human primates and in man.
(v) Zurier and Quagliata (Nature 234: 304, 1971), who describe the inhibitory effect of PGE1 on adjuvant arthritis in rats.
(vi) Zurier, Sayadoff, Torrey and Rothfield (Arthritis Rheum 20: 723, 1977) who describe the inhibitory effect of PGE1 on a naturally occurring inflammatory disease in mice which resembles human systemic lupus erythematosus.

THE PRESENT INVENTION

In the light of the general discussion above, the prior art referred to, and the present inventor's earlier U.S. Patent Application No. 4924 dated 19th January 1979, now U.S. Pat. No. 4,273,763, the present invention in its various aspects may be stated as:

A. A method of treating inflammatory disorders which comprises administering an effective amount of $\gamma$-linolenic acid or other material as above, in conjunction with an effective amount of (a) a material enhancing physiological synthesis of 1-series PGs or (b) a material enhancing physiological synthesis of TXA2, or (c) materials selected from both such groups.

B. A pharmaceutical composition per se comprising $\gamma$-linolenic acid or other material as above in conjunction with (a) a material enhancing physiological synthesis of TXA2, or (b) both such a material and a material selectively enhancing physiological synthesis of 1-series PGs, in an acceptable pharmaceutical vehicle. (Compositions of $\gamma$-linolenic acid etc. as above, in conjunction with zinc and/or $\beta$-lactam antibiotics which are believed to give such 1-series PG enhancement, are the subject, inter alia, of the above U.S. patent application).

C. A method of treating inflammatory disorders which comprises administering an effective amount of $\gamma$-linolenic acid or other material as above, in conjunction with an effective amount of (a) zinc, a $\beta$-lactam antibiotic, penicillamine, phenformin or levamisole, or (b) colchicine, other compounds including vinblastine, vincristine, and other Vinca alkaloids, griseofulvin amantadine, melatonin (pineal hormone) or interferon, or (c) materials selected from both such groups.

D. A pharmaceutical composition per se, comprising $\gamma$-linolenic acid or other material as above, colchicine or other material as above, and optionally zinc or other material as above, alone or in an acceptable pharmaceutical vehicle.

E. A pharmaceutical composition per se, comprising $\gamma$-linolenic acid or other material as above, and penicillamine, phenformin or levamisole.

INFLAMMATORY DISORDERS TREATED

The disorders that can be treated include: multiple sclerosis; systemic lupus erythematosus; Crohn's disease; ulcerative colitis; inflammatory diesease of the kidney, for example, glomerulo-nephritis and nephrotic syndrome; inflammatory and degenerative diseases of the nervous and muscular systems, for example, muscular dystrophies, Friedreich's ataxia and related conditions of peripheral nerve degeneration; disorders of an auto-immune nature; and other collagen related diseases; rheumatoid arthritis and other inflammatory joint disorders; inflammatory skin disorders; disorders characterised by recurrent inflammation such as Familial Mediterranean Fever or Behcet's Syndrome.

PACKS

If it is not desired to have compositions comprising active materials listed above, packs may be prepared comprising the materials presented for separate or part joint and part separate administration in the appropriate relative amounts, and such packs are within the purview of the invention.

DIETARY COMPOSITIONS

The invention is chiefly described in terms of pharmaceutical compositions, but it will be understood that the γ-linolenic and other acids, being in the nature of dietary supplements, could be incorporated in a dietary margarine or other foodstuffs; such foodstuffs, possibly containing other active materials and generally referred to in this description as dietary or pharmaceutical compositions, are within the purview of the invention and thus of the term pharmaceutical compositions, packs or the like used in the claims.

VETERINARY APPLICATIONS

It will be understood that where a disorder of a kind calling for treatment in animals arises, the invention while described primarily in terms of human medicine and treatment is equally applicable in the veterinary field.

AMOUNTS OF ACTIVE MATERIALS

Amounts of zinc and β-lactam antibiotics are given later in general discussion of those materials.

Amounts of the alternative materials penicillamine, phenformin and levamisole are Penicillamine: 50 mg to 10 g/day
Phenformin: 10 mg to 5 g/day
Levamisole: 10 mg to 2 g/day For colchicine, based on present evidence, a suitable dose regimen for inflammatory disorders involves the administration of from 0.3 to 15, for example 0.6 to 2.4 mg, of colchicine per day. Other materials may conveniently be in the following amounts.

amantadine: 100 to 1000 mg/day
griseofulvin: 0.5 to 5 g/day
vinblastine: 0.5 to 5 mg/kg/week (average weight 70 kg)
vincristine: 0.1 to 1.0 mg/kg/week (average weight 70 kg)
interferon (by injection): $1 \times 10^5$ to $1 \times 10^8$ units/day
melatonin: 10 mg to 5 g/day

AMOUNTS OF γ-LINOLENIC AND OTHER ACIDS SPECIFICALLY

A preferred daily dosage for inflammatory disorders for an adult (weight ca 75 kg) is from 0.05 or 0.1 up to 1, 2, 5 or even 10 g as required of γ-linolenic acid or equivalent weight (calculated as γ-linolenic acid) of physiologically functional derivative thereof. Amounts may in particular be 0.1 to 1.0 g daily. Such doses correspond to about 2 to 20 g daily of the Oenothera oil discussed below. In place of, or in addition to, γ-linolenic acid, one may use dihomo-γ-linolenic acid or a physiologically functional derivative thereof, in amounts equivalent in molar terms to γ-linolenic acid and calculated as such. This dosage can for example be taken as a single dose or divided into 2, 3 or 4 subdivisions thereof as convenient.

Again based on present evidence, a particularly suitable daily dosage in inflammatory disorders for an adult (weight ca 75 kg) would be from 0.1 to 1.0 g of γ-linolenic acid or equivalent weight of functional derivative thereof.

FORMS AND SOURCES OF γ-LINOLENIC AND OTHER ACIDS

Convenient physiologically functional derivatives of γ-linolenic acid and dihomo-γ-linolenic acid for use according to the invention for all the purposes described include the $C_1$–$C_4$ alkyl (e.g. methyl and ethyl) esters and the glycerides of the acids.

If desired, pharmaceutical compositions may be produced for use in the invention by associating natural or synthetic γ-linolenic acid (or a physiologically functional derivative thereof) and/or dihomo-γ-linolenic acid (or a physiologically functional derivative thereof), as such, with an acceptable pharmaceutical vehicle. It is at present convenient to incorporate the γ-linolenic acid into compositions in the form of an available oil having a high γ-linolenic acid content.

At the present time known natural source of oils having a high γ-linolenic acid content are few (there are no known natural sources of significant amounts of dihomo-γ-linolenic acid). One source of oils currently available is the seed of Evening Primrose species such as *Oenothera biennis L.* and *Oenothera lamarckiana*, the oil extract therefrom containing γ-linolenic acid (about 8%) and linoleic acid (about 72%) in the form of their glycerides together with other glycerides (percentages based on total fatty acids). Another source of γ-linolenic acid is the seed of Borage species such as *Borago officinalis* which, though its current yield per acre is low, provides a richer source of γ-linolenic acid than Oenothera oil. Recent studies on fungi which can be cultivated by fermentation promise a fungal oil source.

The seed oil extracts referred to above can be used as such or can for example if desired be fractionated to yield an oily composition containing the triglycerides of γ-linolenic acid and linoleic acid as the main fatty acid components, the γ-linolenic acid content being if desired a major proportion. Seed oil extracts appear to have a stabilising effect upon any dihomo-γ-linolenic acid or physiologically functional derivative thereof incorporated therein.

USE OF ZINC

Without restriction to the theory, it is believed that zinc tends to stimulate the biosynthesis of 1 series PG's and specifically that it potentiates mobilisation of esterified reserves of dihomo-γ-linolenic acid. This enables one to use zinc conjointly with γ-linolenic acid and/or dihomo-γ-linolenic acid. The presence of arachidonic acid or any other material tending to oppose the PG 1 enhancing effect is, naturally, to be avoided.

Based on present evidence, a suitable daily dosage for an adult (weight ca 75 kg) is 2.5–800 mg preferably 10–200 mg and advantageously 10–80 mg zinc daily, with γ-linolenic acid or other acid or equivalent in the amounts previously discussed. The 10–80 mg zinc is approximately 0.125–1.0 mg/kg adult body weight. In view of the conjoint effect of the zinc preferred amounts of γ-linolenic or other acid or equivalent are less than when zinc is not present, advantageously 0.1 to 1.0 g daily. As before the dosage can be taken as a single dose or divided into 2, 3 or 4 subdivisions thereof.

Conveniently the zinc and γ-linolenic or other acid or derivatives are given together in a single preparation but they can of course be taken separately.

The zinc should be administered in a form in which it is readily taken up in vivo. Ordinarily this will indicate the use of a zinc salt of a mineral or organic acid, said salt being physiologically acceptable at the given dosage. Some zinc salts which would be contraindicated at higher dosages may be satisfactory for present purposes at the dosages indicated above. Useful salts include zinc sulphate and zinc gluconate and in particular zinc oleate, γ-linolenate and dihomo-γ-linolenate, and zinc oxide may also be employed. It is also possible to administer the zinc in chelated form. In any event, the preferred amounts of zinc are as stated above (the quantities given being calculated as zinc metal). Zinc oleate may be made by the method disclosed in Monatschrift 42 287 (1921) and similar methods may be applied to make for example zinc γ-linolenate if desired.

EXPERIMENTAL WORK ON USE OF ZINC

In one group of experiments the test preparation was the isolated superior mesenteric vascular bed, taken from male rats as for example described in the Canadian J. Physiol Pharmacol 54:357, 1976. The perfusion flow rate was at a constant value between 3 to 4 ml/min., pressure 25 to 30 mm Hg, using Krebs bicarbonate buffer containing in nM 150 Na, 4.3 K, 1.0 mg, 2.5 Ca, 1.7 phosphate, 25 bicarbonate and 11.1 glucose.

Prior to testing the basic vasoconstrictive effect of norepinephrine. as the bitartrate, in successive 10 ng amounts was established, as the amplitude of a transient rise of about 1 min in the perfusion pressure.

Zinc, as the chloride, was then added to the perfusion buffer at successive concentrations and the norepinephrine response measured after 15 minutes at each.

The following results were obtained:

| Zinc concentration (μg/ml) | Response as % of basic level |
|---|---|
| 0.1 | 112 |
| 0.2 | 118 |
| 0.4 | 130 |
| 0.8 | 138 |

In the presence of 50 μg/ml of indomethacin, a known blocking agent for PG synthesis, used with 10 ng/ml PGE 2 to give apparently normal vascular reactivity, the zinc had no effect on the norepinephrine response.

Similar tests with dihomo-γ-linolenic acid and PGE 1 gave respective rises up to a maximum of 130% of the basic response at 50 ng/ml of the acid and a maximum of 150% of the basis response at $2.8 \times 10^{-11}$ M PG.

The results show that zinc gives responses like those of dihomo-γ-linolenic acid and of PGE 1, responses moreover which are not given when PG synthesis is blocked and PGE 2 supplied, and thus the conditions treated with γ-linolenic acid (and thus effectively with dihomo-γ-linolenic acid) may be enhanced in the direction of 1 series PG synthesis by the addition of zinc.

Analogous experiments with the same preparation show that phenformin, levamisole, penicillin and penicillamine have actions consistent with stimulation of PGE 1 synthesis.

USE OF ZINC WITH OTHER MATERIALS

As shown above, in the perfused mesenteric vascular bed of the rat, zinc appears to increase the formation of PGE 1 from DGLA. The presence of either colchicine (100 ng/ml) or melatonin (10 ng/ml) in the perfusion fluid increases the effect of zinc on PGE 1 by 10 to 100 times, the size of the effect depending on the time of the year and being greater in the summer months than in the winter. This is probably because the production of melatonin from the pineal gland is lower in the summer than in the winter and the effect of extra melatonin can therefore be more easily seen in the summer. Colchicine and melatonin appear to act at the same sites in cells, and their overall effect therefore is to increase the formation of PGE 1. The effect is believed to be mediated at least in part by the effect of colchicine and melatonin on thromboxane A2. The alternative materials to colchicine previously mentioned may be expected to have similar effects.

USE OF β-LACTAM ANTIBIOTICS

β-lactam antibiotics which may be used according to the present invention, are conveniently any of the known penicillin and cephalosporin antibiotics (including semi-synthetic antibiotics) such as, for example, penicillin G, penicillin N, penicillin V, cephalexin, cephalothin, ampicillin, amoxycillin, cloxacillin and cephaloglycin. Any of these may be used in the form of their physiologically functional non-toxic derivatives, for example alkali metal salts e.g. sodium and potassium salts, and salts with organic bases, and reference to an antibiotic herein (including the claims) includes reference to such derivatives.

Suitable daily dosages may for example be in the range 0.5 to 10.0 g per day in patients of average weight. Such daily dosages may conveniently be divided as for zinc.

The use of penicillins in long term treatments is especially desirable in view of the known relative absence of side effects of these drugs. Thus, penicillin has been administered for many years to patients having rheumatic heart disease in order to prevent streptococcal infections, and there is virtually no evidence of long term toxicity.

Care should of course be taken to ensure that the patient is not allergic to the drug of choice.

It is believed that the reason for the effectiveness of the antibiotics in certain disorders is that they enhance utilisation of ester reserves of dihomo-γ-linolenic acid. Whether or not this is so, and no restriction to the theory is intended, zinc and antibiotics do appear to have parallel effects in treating all the conditions discussed herein when used with the γ-linolenic or other acids and derivatives.

In particular in tests carried out on the rat mesenteric bed system as above, both penicillin V and penicillin G have given responses similar in kind and degree to those given for zinc, supporting further inventor's belief that β-lactam antibiotics are of value in all other conditions treated according to the invention in similar way to the action of zinc. It may be expected that colchicine will enhance the effect of antibiotics just as it enhances the zinc effect.

PHARMACEUTICAL PRESENTATION

The compositions according to the invention are conveniently in a form suitable for oral, rectal, parenteral or topical administration in a suitably pharmaceutical vehicle, as discussed in detail for example in U.K. Patent Specification No. 1 082 624 and in any case very well known generally for any particular kind of preparation. Thus for example tablets, capsules, ingestible liquid or powder preparations, creams and lotions for topical application, or suppositories, can be prepared as required. Injectable solutions of hydrolysed Oenothera oil may be prepared using albumin to solubilise the free acid.

Advantageously a preservative is incorporated into the preparations. $\alpha$-Tocopherol in a concentration of about 0.1% by weight has been found suitable for the purpose.

It will be understood that the absolute quantity of active ingredients present in any dosage unit should not exceed that appropriate to the rate and manner of administration to be employed but on the other hand should also desirably be adequate to allow the desired rate of administration to be achieved by a small number of doses. The rate of administration will moreover depend on the precise pharmacological action desired.

The following Examples serve to illustrate pharmaceutical compositions useful in treatment according to the invention:

EXAMPLES

Pharmaceutical compositions containing a unit dose of an oil extract from the seeds of *Oenothera biennis L.* optionally with methyl dihomo-$\gamma$-linolenate and/or zinc sulphate and/or penicillin V and/or any of the other active materials referred to herein are prepared by encapsulation of the natural oil in soft gelatin capsules manufactured by known methods.

The oil is extracted from the seeds by one of the conventional methods of extraction such as cold pressure, screw pressure after partially cooking the seed, or solvent extraction.

Fractionation of a typical sample of this oil shows a yield of 97.0% oil in the form of methyl esters, with the relative proportions:

Palmitate: 6.15
Stearate: 1.6
Oleate: 10.15
Linoleate: 72.6
$\gamma$-Linolenate: 8.9

As preservative, $\alpha$-tocopherol is added to the oil in a concentration of 0.1%.

Gelatin capsules containing oil extracts prepared as described above, each having the following contents of active ingredients (0.5 g oil extract = ca 0.045 g $\gamma$-linolenic acid), are prepared in conventional fashion.

EXAMPLE 1

Oil extract: 0.5 g
Zinc sulphate: 10 mg
Two capsules may be administered thrice daily in the treatment of inflammatory disorders as above, giving a daily dose of $\gamma$-linolenic acid of ca 0.27 g.

EXAMPLE 2

Oil extract: 0.5 g
Methyl dihomo-$\gamma$-linolenate: 10 mg
Zinc sulphate: 20 mg
Two capsules may be administered thrice daily in the treatment of inflammatory disorders as above.

EXAMPLE 3

Oil extract: 0.5 g
Penicillin V: 0.25 g
Two capsules may be administered thrice daily in the treatment of inflammatory disorders as above. Levamisole 25 mg, penicillamine 100 mg or phenformin 25 mg are alternatives to penicillin.

EXAMPLE 4

Oil extract: 0.5 g
Penicillin V: 0.25 g
Zinc sulphate: 10 mg
Two capsules may be administered thrice daily in the treatment of inflammatory disorders as above. Levamisole 25 mg, penicillamine 100 mg or phenformin 25 mg are alternatives to penicillin.

EXAMPLE 5

Oil extract: 0.5 g
Methyl dihomo-$\gamma$-linolenate: 10 mg
Penicillin V: 0.25 g
Zinc sulphate: 10 mg
Two capsules may be administered thrice daily in the treatment of inflammatory disorders as above.

EXAMPLE 6

Oil extract: 0.5 g
Methyl dihomo-$\gamma$-linolenate: 10 mg
Two capsules may be administered twice daily in the treatment of inflammatory disorders as above.

EXAMPLE 7

Oil extract: 0.5 g
Colchicine: 0.15 mg
One capsule may be administered four times daily in the treatment of multiple sclerosis and other inflammatory disorders as described above.

EXAMPLE 8

Oil extract: 0.5 g
Methyl dihomo-$\gamma$-linolenate: 10 mg
Colchicine: 0.3 mg
One capsule may be administered four times daily in the treatment of multiple sclerosis and other inflammatory disorders as described above.

EXAMPLE 9

Oil extract: 0.5 g
Colchicine: 0.25 mg
Penicillin V: 0.25 g
One or two capsules may be administered four times daily in the treatment of multiple sclerosis and other inflammatory disorders as described above.

EXAMPLE 10

Oil extract: 0.5 g
Colchicine: 0.25 mg
Zinc oleate: 20 mg
One or two capsules may be administered four times daily in the treatment of multiple sclerosis and other inflammatory disorders as described above.

EXAMPLE 11

Oil extract: 0.5 g
Phenformin: 25 mg

Amantadine: 100 mg

One or two capsules may be administered four times daily in the treatment of multiple sclerosis and other inflammatory disorders as described above.

EXAMPLE 12

Oil extract: 0.5 g
Colchicine: 0.25 mg
Levamisole: 25 mg

One or two capsules may be administered four times daily in the treatment of multiple sclerosis and other inflammatory disorders as described above.

EXAMPLE 13

Oil extract: 0.5 g
Colchicine: 0.25 mg
Penicillamine: 100 mg

One or two capsules may be administered four times daily in the treatment of multiple sclerosis and other inflammatory disorders as described above.

EXAMPLE 14

Oil extract: 0.5 g
Griseofulvin: 0.5 mg

One capsule may be administered four times daily in the treatment of multiple sclerosis and other inflammatory disorders as described above.

EXAMPLE 15

Oil extract capsules or oil extract plus zinc capsules may be administered as in Example 1 in conjunction with 70 mg/week vinblastine.

EXAMPLE 16

Oil extract capsules or oil extract plus zinc capsules may be administered as in Example 1 in conjunction with 70 mg/week vincristine.

EXAMPLE 17

Oil extract capsules or oil extract plus zinc capsules may be administered as in Example 1 in conjunction with 0.5 g/day melatonin.

EXAMPLE 18

Oil extract capsules or oil extract plus zinc capsules may be administered as in Example 1 in conjunction with $1 \times 10^6$ units/day interferon.

FURTHER EVIDENCE-INFLAMMATORY DISORDERS

In inflammatory disorders in animals PGE 1 is able to improve the conditions successfully (prior art (v) and (vi)). It may therefore be expected that agents which enhance endogenous formation of PGE 1 will have a similar effect. Indeed this may be how penicillamine and levamisole work in rheumatoid arthritis although this has not been suggested other than by the present inventor.

Dosages in the claims hereafter are daily unless otherwise stated.

What is claimed is:

1. A pharmaceutical composition useful for the treatment of inflammatory disorders comprising: (a) an effective amount of γ-linolenic acid or physiologically functional derivative thereof and/or dihomo-γ-linolenic acid or physiologically functional derivative thereof, and (b) an effective, conjoint amount of another material enhancing the synthesis or action of thromboxane A2, alone or in an acceptable pharmaceutical vehicle.

2. A pharmaceutical composition useful for the treatment of inflammatory disorders comprising: (a) an effective amount of γ-linolenic acid or physiologically functional derivative thereof and/or dihomo-γ-linolenic acid or physiologically functional derivative thereof, and (b) an effective, conjoint amount of a material selected from colchicine, vinblastine, vincristine, and other Vinca alkaloids, griseofulvin, amantadine, melatonin, and interferon, alone or in an acceptable pharmaceutical vehicle.

3. The composition of claim 1 or 2, presented for administration in doses comprising 0.05 to 10 g of (a) calculated as γ-linolenic acid, or one half one third or one quarter of said amount.

4. The composition of claim 1 or 2, presented for administration in doses comprising 0.1 to 1 g of (a) calculated as γ-linolenic acid or one half one third or one quarter of said amount.

5. The composition of claim 2, presented in daily or where specified weekly doses for administration in doses comprising:
   0.3 to 15 mg colchicine or
   100 to 1000 mg amantidine or
   0.5 to 5 g griseofulvin or
   35 to 350 mg vinblastine (weekly) or
   7 to 70 mg vincristine (weekly) or
   $1 \times 10^5$ to $1 \times 10^8$ units interferon or
   10 mg to 5 g melatonin
or one half one third or one quarter of said amount.

6. A pharmaceutical composition useful for the treatment of inflammatory disorders comprising (a) an effective amount of γ-linolenic acid or physiologically functional derivative thereof and/or dihomo-γ-linolenic acid or physiologically functional derivative thereof, and (b) an effective, conjoint amount of a material selected from penicillamine, phenformin and levamisole, alone or in an acceptable pharmaceutical vehicle.

7. The composition of claim 6, presented for administration in doses comprising 0.05 to 10 g of (a) calculated as γ-linolenic acid, or one half one third or one quarter of said amounts.

8. The composition of claim 6, presented for administration in doses comprising 0.1 to 1 g of (a) calculated as γ-linolenic acid, or one half one third or one quarter of said amounts.

9. The composition of claim 6, presented for administration in doses comprising:
   50 mg to 10 g: penicillamine or
   10 mg to 5 g: phenformin or
   10 mg to 2 g: levamisole
or one half one third or one quarter of said amount.

10. The composition of claim 1, comprising further (c) a conjoint amount of a material influencing the 1-series/2-series PG balance in the body in favor of the 1-series PG's.

11. The composition of claim 2, comprising further (c) a conjoint amount of physiologically assimilable zinc, penicillamine, phenformin, levamisole or a β-lactam antibiotic.

12. The composition of claim 11, wherein the antibiotic is a natural or semi-synthetic penicillin or cephalosporin antibiotic.

13. The composition of claim 11, wherein the antibiotic is selected from penicillin G, penicillin N, penicillin V, cephalothin, ampicillin, amoxycillin, cloxacillin, cephalexin and cephaloglycin.

14. The composition of claim 11, 12 or 13 presented for administration in doses comprising 0.5 to 3 g of the antibiotic or one half one third or one quarter of said amount.

15. The composition of claim 11, presented for administration in doses comprising:
50 mg to 10 g: penicillamine or
10 mg to 5 g: phenformin or
10 mg to 2 g: levamisole
or one half one third or one quarter of said amount.

16. The composition of claim 11, presented for administration in doses comprising 2.5 to 800 mg assimilable zinc calculated as the metal, or one half one third or one quarter thereof.

17. The composition of claim 11, presented for administration in doses comprising 10 to 200 mg assimilable zinc calculated as the metal, or one half one third or one quarter thereof.

18. The composition of claim 11, presented for administration in doses comprising 10 to 80 mg assimilable zinc calculated as the metal, or one half one third or one quarter thereof.

19. A composition according to claim 11 wherein the zinc is present as a zinc oleate, γ-linolenate or dihomo-γ-linolenate.

20. A method of treating inflammation, comprising administering to a person suffering therefrom an effective amount of γ-linolenic acid or a physiologically functional derivative thereof and/or dihomo-γ-linolenic acid or a physiologically functional derivative thereof, and an effective conjoint amount of a material influencing the 1-series/2-series PG balance in the body in factor of the 1-series PG's.

21. A method of treating inflammation, comprising administering to a person suffering therefrom an effective amount of γ-linolenic acid or a physiologically functional derivative thereof and/or dihomo-γ-linolenic acid or a physiologically functional derivative thereof, and an effective conjoint amount of a material selected from physiologically assimilible zinc, penicillamine, phenformin, levamisole, or a βγ-lactam antibiotic.

22. A method of treating inflammation, comprising administering to a person suffering therefrom an effective amount of γ-linolenic acid or a physiologically functional derivative thereof and/or dihomo-γ-linolenic acid or a physiologically functional derivative thereof and an effective conjoint amount of a material enhancing synthesis or action of thromboxane A2.

23. A method of treating inflammation, comprising administering to a person suffering therefrom an effective amount of γ-linolenic acid or a physiologically functional derivative thereof and/or dihomo-γ-linolenic acid or a physiologically functional derivative thereof and/or dihomo-γ-linolenic acid or a physiologically functional derivative thereof and an effective conjoint amount a material selected from colchicine, vinblastine, vincristine and other Vinca alkalodis, griseofulvin, amantadine, melatonin, and interferon.

24. A method of treating inflammation, comprising administering to a person suffering therefrom (1) an effective amount of γ-linolenic acid or a physiologically functional derivative thereof and/or dihomo-γ-linolenic acid or physiologically functional derivative thereof, (2) an effective conjoint amount of physiologically assimilable zinc, penicillamine, phenformin, levamisole, or a β-lactam antibiotic, and (3) an effective conjoint amount of a material selected from colchicine, vinblastine, vincristine and other Vinca alkaloids, griseofulvin, amantadine, melatonin, and interferon.

25. A method according to claim 21, wherein said antibiotic is a natural or semi-synthetic penicillin or cephalosporin antibiotic.

26. A method according to claim 25, wherein said antibiotic is selected from penicillin G, penicillin N, penicillin V, cephalothin, ampicillin, amoxycillin, cloxacillin, cephalexin and cephaloglycin.

27. A method according to claim 20, wherein the daily amount of said acid or derivative is 0.05 to 10 g calculated as γ-linolenic acid.

28. A method according to claim 27, wherein the daily amount of said acid or derivative is 0.1 to 5 g.

29. A method according to claim 21, wherein the daily amount of said zinc is 2.5 to 800 mg calculated as the metal.

30. A method according to claim 29, wherein the amount of zinc is 10 to 200 mg.

31. A method according to claim 29, wherein the amount of zinc is 10 to 80 mg.

32. A method according to claim 21, wherein the daily amount of said penicillamine, phenformin or levamisole is
50 mg to 10 g pencillamine or
10 mg to 5 g phenformin or
10 mg to 2 g levamisole.

33. A method according to claim 21, 25, or 26, wherein the daily amount of said antibiotic is 0.3 to 5 g.

34. A method according to claim 22, further comprising administering an effective, conjoint amount of a material influencing the 1-series/2-series PG balance in the body in favor of 1-series PG's.

35. A method according to claim 23, further comprising administering an effective, conjoint amount of a material influencing the 1-series/2-series PG balance in the body in favor of 1-series PG's.

36. A method according to claim 23 or 35 when said selected material is administered in a daily or where specified weekly amount of:
0.3 to 15 mg colchicine or
100 to 1000 mg amantadine or
0.5 to 5 g griseofulvin or
35 to 350 mg vinblastine (weekly) or
7 to 70 mg vincristine (weekly) or
$1 \times 10^5$ to $1 \times 10^8$ units interferon or 10 mg to 5 g melatonin 37. A method according to claim 21 in which said zinc is in the form of zinc oleate, γ-linolenate or dihomo-γ-linolenate.

* * * * *

UNITED STATES PATENT AND TRADEMARK OFFICE
CERTIFICATE OF CORRECTION

PATENT NO. : 4,309,415
DATED : January 5, 1982
INVENTOR(S) : David F. HORROBIN

It is certified that error appears in the above-identified patent and that said Letters Patent are hereby corrected as shown below:

Page 1, [73] delete "Verronmay Limited" insert

--Efamol Limited--.

Signed and Sealed this

Tenth Day of August 1982

[SEAL]

Attest:

GERALD J. MOSSINGHOFF

Attesting Officer

Commissioner of Patents and Trademarks